United States Patent [19]

Ehr et al.

[11] Patent Number: 4,670,045
[45] Date of Patent: Jun. 2, 1987

[54] FUNGICIDAL CONTROL EMPLOYING ESTER DERIVATIVES OF 4,6-DISUBSTITUTED 2-PYRIDINOLS

[75] Inventors: Robert J. Ehr, Eden Prairie, Minn.; Helen K. Tobol, Concord; Lillian H. Troxell, Antioch, both of Calif.

[73] Assignee: The Dow Chemical Company, Midland, Mich.

[21] Appl. No.: 748,796

[22] Filed: Jun. 26, 1985

Related U.S. Application Data

[63] Continuation-in-part of Ser. No. 548,750, Nov. 4, 1983, abandoned, and a continuation-in-part of Ser. No. 548,269, Nov. 3, 1983, abandoned, and a continuation-in-part of Ser. No. 548,751, Nov. 4, 1983, abandoned.

[51] Int. Cl.$^4$ .................... A01N 43/40; C07D 211/84
[52] U.S. Cl. ......................................... 71/94; 546/295; 546/300; 546/302
[58] Field of Search ............. 546/300, 302, 295; 71/94

[56] References Cited

U.S. PATENT DOCUMENTS

| | | | |
|---|---|---|---|
| 3,207,760 | 9/1965 | Brown | 546/300 |
| 3,244,722 | 4/1966 | Johnston et al. | 546/300 |
| 3,317,542 | 5/1967 | Harreldine et al. | 546/300 |
| 3,535,324 | 10/1970 | Hamer | 546/300 |
| 3,682,936 | 8/1972 | Tarba et al. | 546/303 |
| 3,705,170 | 12/1972 | Torba et al. | 546/300 |
| 3,711,486 | 1/1973 | Torba | 546/300 |
| 3,983,238 | 9/1976 | Morisawa et al. | 546/300 |
| 4,062,962 | 12/1977 | Noveroske | 546/300 |
| 4,143,144 | 3/1979 | Tobol et al. | 546/300 |

FOREIGN PATENT DOCUMENTS

| | | | |
|---|---|---|---|
| 782599 | 1/1966 | Canada | 546/300 |
| 1184876 | 3/1970 | United Kingdom | 546/300 |

OTHER PUBLICATIONS

Abramovitch, Pyridine and Its Derivatives Part 3, pp. 732–208.
Melrikov, N. N. Chemistry of Pesticides (1977) p. 404.
Cava et al., Pyridine Derivatives, vol. 23, pp. 1616–1617.
Hamer et al., Synthesis and Nematocidal Activity of 2-Pyridyl Alkanesulfonates, J. Arg Food Chem. (1978), pp. 57–60.

*Primary Examiner*—John M. Ford
*Assistant Examiner*—J. Richter
*Attorney, Agent, or Firm*—S. Preston Jones; Ronald G. Brookens

[57] ABSTRACT

6-Halo(or $CF_3$)-4-((di- or tri)halomethyl)-2-pyridinyl esters of carboxylic, carbonic, carbamic, thiocarbamic, sulfonic, or sulfamic acids, exemplified by 6-chloro-4-(trichloromethyl)-2-pyridinyl pentanoate, 4-methylbenzenesulfonate or methylcarbamate, are novel and are useful in the protection of plants from attack by soil-borne fungi.

39 Claims, No Drawings

FUNGICIDAL CONTROL EMPLOYING ESTER DERIVATIVES OF 4,6-DISUBSTITUTED 2-PYRIDINOLS

CROSS-REFERENCE TO RELATED APPLICATIONS

This application is a continuation-in-part of Ser. No. 548,750 filed on Nov. 4, 1983 now abandoned, and incorporates the claimed subject matter of Ser. No. 548,269 filed Nov. 3, 1983 now abandoned and Ser. No. 548,751 filed Nov. 4, 1983, now abandoned.

DESCRIPTION OF THE PRIOR ART

In U.S Pat. No. 3,244,722 compounds corresponding to the formula

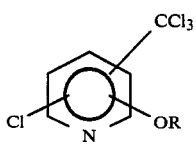

wherein R is alkyl of 1 to 18 carbon atoms or lower alkenyl are taught.

As reported in this patent, various compounds disclosed therein are useful as herbicides; various other compounds are useful in the control of pest fish and aquatic insects; and other compounds are taught to be useful as insecticides and anthelmintic agents for warm-blooded animals.

In U.S. Pat. No. 4,062,962, a select group of the compounds taught in U.S. Pat. No. 3,244,722 are taught as fungicides for the control of soil-borne plant disease organisms which attack the roots of plants.

In U.S. Pat. No. 3,983,238, there are described and claimed compounds having anticoccidal activity and of the formula

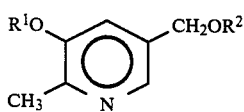

wherein $R^1$ and $R^2$ are each hydrogen, aliphatic acyl, aromatic acyl or heterocyclic acyl with at least $R^1$ or $R^2$ being heterocyclic acyl.

Other related known prior art includes U.S. Pat. No. 3,317,542 which is directed to compounds of the formula

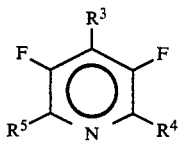

wherein $R^3 R^4$ and $R^5$ may be the same or different and each represents a list of groups including alkoxy and methyl. The utility of these compounds is not set forth.

In U.S. Pat. Nos. 3,705,170 and 3,711,486 compounds of the formula

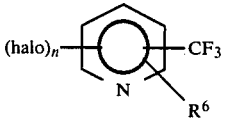

wherein $(halo)_n$ is 0, 1, 2 or 3 chloro or fluoro groups and $R^6$ is hydroxy, mercapto, amino, alkylamino, hydrazino, alkylhydrazino, alkylthio(or sulfonyl), alkoxy, alkenyloxy, aryloxy, arylthio(or sulfonyl), oxyloweralkanoic acid and derivatives thereof including the alkyl ester. These compounds are taught as herbicides, miticides, anthelmintics, fungicides and bactericides.

SUMMARY OF THE INVENTION

The present invention is directed to compounds, compositions containing compounds, and the use as fungicides of compounds corresponding to the formula

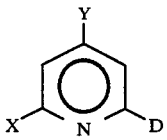

wherein
X represents bromo, chloro, fluoro, iodo or trifluoromethyl;
Y represents —CCl$_3$, —CF$_3$, —CHCl$_2$, —CFCl$_2$ or —CF$_2$Cl;
D represents

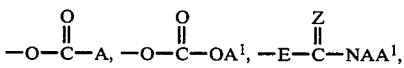

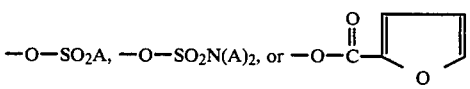

wherein Z represents oxygen or sulfur; E represents oxygen or sulfur with the proviso that E can be sulfur only if Y is CF$_3$; each A independently represents hydrogen, alkyl of 1 to 4 carbon atoms, alkenyl of 2 to 4 carbon atoms, phenyl or benzyl and $A^1$ represents alkyl of 1 to 4 carbon atoms, alkenyl of 2 to 4 carbon atoms, phenyl or benzyl.

In the present specification and claims, the terms "alkyl" designates straight chain, saturated aliphatic groups of 1 to 4 carbon atoms and branched chain and cyclic saturated aliphatic groups of 3 or 4 carbon atoms, inclusive, such as, for example, methyl, ethyl, propyl, isopropyl, cyclopropyl, butyl, secondary-butyl, tertiary-butyl or cyclobutyl. The above groups may be substituted with 1 or 2 groups, such as chloro, bromo, fluoro, nitro or cyano. In addition, the phenyl and benzyl groups can also be ring substituted with 1 or 2 groups, such as, chloro, fluoro, bromo, C$_1$-C$_4$ alkyl, nitro or cyano.

The pyridine compounds of the present invention are crystalline solids or oils and are of low solubility in water and of moderate solubility in common organic solvents.

The pyridine compounds of the present invention and compositions containing said compounds have been found useful, as agronomic fungicides, especially useful and valuable for the control of soil-borne plant root disease organisms The compounds of the present invention can be prepared employing a variety of different procedures. In the preparation of specific compounds, one preparative procedure may be considered to be more appropriate than another. The choice of the specific preparative procedure to use will be dependent on a variety of reasons such as, for example, the specific starting materials available, the reaction conditions to be employed, the specific final product to be prepared, the amount of final product needed and the like.

The compounds of the present invention can be prepared by the reaction of an appropriate halomethyl substituted pyridine reactant of the formula

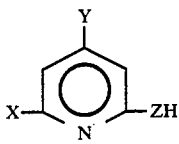

wherein X, Y and Z are as hereinbefore defined with an appropriate acid halide of an appropriate carbonic acid, carbamic acid, thiocarbamic acid, carboxylic acid, sulfonic acid or sulfamic acid of the formula Hal—G wherein Hal is chloro, fluoro or bromo, G is

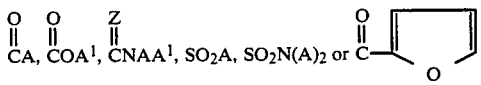

and A, A$^1$, and Z are as hereinabove defined in the presence of a reaction medium and a hydrogen halide acceptor (i.e., acid-binding agent). This reaction can be represented as follows:

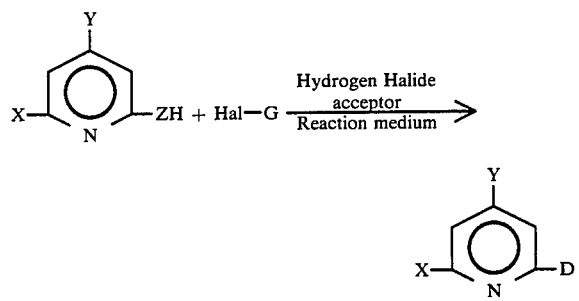

No attempt has been made to present a balanced equation.

In carrying out the above reaction, the appropriate halomethyl substituted pyridine reactant is mixed with the acid halide of the appropriate carboxylic acid, carbonic acid, carbamic acid, thiocarbamic acid, sulfonic acid, or sulfamic acid reactant in the presence of the reaction medium and the hydrogen halide acceptor at a temperature of from about 20° C. up to the reflux temperature of the mixture until the reaction is complete. The reaction is usually complete in from about 1 to 48 hours, depending upon the specific reactants and solvents employed.

Suitable hydrogen halide absorbers (i.e., acid-binding agents) are, for example, organic amines such as triethylamine, dimethylaniline, or pyridine, inorganic bases such as the hydroxides and carbonates of alkali metals and alkaline earth metals, such as sodium, potassium, calcium, or lithium. These agents are employed in from about an equimolar amount up to about a 10 percent excess based on the acid halide reactant.

After the completion of the reaction, the reaction mixture is usually filtered and the solvent (reaction medium) is removed by evaporation. Alternatively, the reaction mixture is diluted with water and extracted with a solvent such as methylene chloride, petroleum ether, hexane or toluene. The extract is thereafter usually washed with water, dried, filtered and the solvent removed by evaporation or other conventional separatory procedures. The product is thereafter recovered, and, if desired, can be further purified by various conventional techniques such as crystallization and/or recrystallization from solvents such as, for example, methanol, methylene chloride, hexane, or toluene or by distillation depending upon whether the product is a solid or oil.

In an alternative procedure, an appropriate halomethyl substituted halopyridine reactant is mixed with an appropriate alkaline earth or alkali metal salt of the appropriate carboxylic acid, carbonic acid, carbamic acid, thiocarbamic acid, sulfonic acid, or sulfamic acid reactant. The preparation of such salts are well known. This reaction can be represented as follows:

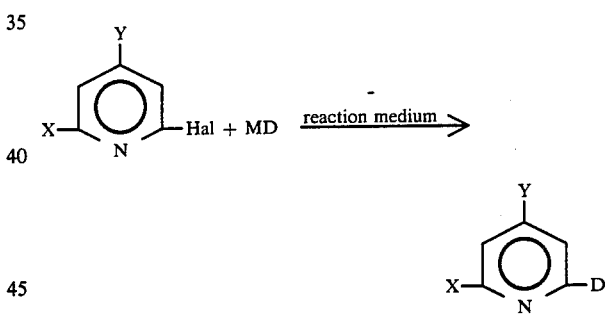

wherein X, Y, Hal and D are as hereinabove defined and M is one of the alkaline earth or alkali metals set forth hereinbefore.

In carrying out the above procedures, the reaction conditions and the product recovery procedures are the same as set forth above.

The reaction consumes the reactants in stoichiometric proportions, i.e., one molar equivalent of the halopyridine reactant to one molar equivalent of the salt reactants. An excess of the salt reactant can be employed.

Representative solvents for use in carrying out the above reactions include dimethyl sulfoxide, dimethylformamide, N-methyl-2-pyrrolidone, toluene, dimethoxyethane and xylene.

For the preparation of compounds wherein D is

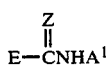

an appropriate halomethyl substituted pyridine reactant of the formula

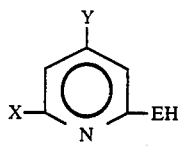

wherein E X, Y and Z are as hereinbefore defined is reacted with an appropriate alkyl, alkenyl, phenyl or benzyl isocyanate or isothiocyanate of the formula $$A^1NC=Z$$

in the presence of a solvent and an amine catalyst. This reaction can be represented as follows:

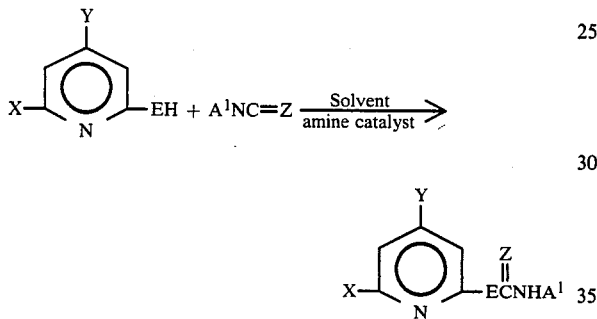

wherein $A^1$, E, X, Y and Z are as hereinbefore defined. No attempt has been made to present a balanced equation.

In carrying out the above procedures, the reaction conditions and the product recovery procedures are the same as set forth above.

The reaction consumes the reactants in stoichiometric proportions, i.e., one molar equivalent of the halopyridine reactant to one molar equivalent of the isocyanate or isothiocyanate reactant. A 5 to 25 percent excess of the latter reactant can be employed.

Representative solvents for use in carrying out the above reactions include dimethyl sulfoxide, dimethylformamide, N-methyl-2-pyrrolidone, toluene, dimethoxyethane and xylene.

DESCRIPTION OF SOME PREFERRED EMBODIMENTS

In order that the present invention may be more fully understood, the following examples are given primarily by way of illustration and should not be construed as limitations upon the overall scope of the present invention.

EXAMPLE 1

6-Chloro-4-(trichloromethyl)-2-pyridinyl ethyl carbonate

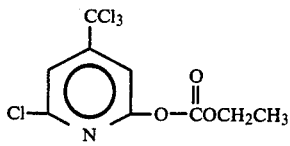

A solution was prepared by dissolving 6.17 grams (g) (0.025 mole (m)) of 2-chloro-6-hydroxy-4-(trichloromethyl)pyridine in 100 milliliters of toluene. To this solution was added 2.53 g (0.025 m) of triethylamine. To this mixture was then added 2.71 g (0.025 m) of ethyl chloroformate dissolved in 20 ml of toluene. The mixture was stirred at 50° C. for 4 hours. The salt which formed was removed by filtration and the toluene was removed by evaporation under reduced pressure. Using a short path distillation (Kugelrohr) at 130° C. and 80 millimeters of mercury, 6-chloro-4-(trichloromethyl)-2-pyridinyl ethyl carbonate was obtained in a yield of 6.65 g (83 percent of theory). The product had a refractive index of $n(25/d)=1.5354$. The structure of the product was confirmed by its NMR spectrum (Compound No. 1).

EXAMPLE 2

6-Chloro-4-(trichloromethyl)-2-pyridinyl methylcarbamate

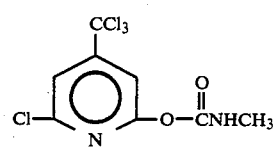

A solution was prepared by dissolving 7.4 g (0.03 m) of 6-chloro-4-(trichloromethyl)-2-pyridinol in 45 ml of dry dimethylformamide. To this solution was added 1.71 g (0.03 m) of methyl isocyanate and 7 drops of triethylamine. The mixture was allowed to stand, at room temperature, for ~30 hours. The reaction mixture was then poured over ice and the resulting solids were filtered out and taken up in hexane. The above-named product was recrystallized from the hexane and recovered in a yield of 3.8 g. The product melted at 95.5°–99.5° C. The structure of the compound was confirmed by its IR spectrum. Upon analysis, the product was found to have carbon, hydrogen, nitrogen and chlorine contents of 31.90, 2.10, 9.10 and 46.26 percent, respectively, as compared with the theoretical contents of 31.50, 1.99, 9.22 and 46.50 percent, respectively, as calculated for the above-named compound (Compound 2).

By following the above preparative procedures, the following compounds are prepared.

TABLE I

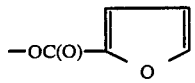

| Compound Number | X | Y | D | Physical Properties* |
|---|---|---|---|---|
| 3 | —Cl | —CCl₃ | —OC(O)n-C₄H₉ | RI = 1.5330 |
| 4 | —Br | —CF₃ | —OC(O)n-C₄H₉ | |
| 5 | —F | —CFCl₂ | —OC(O)CH₃ | |
| 6 | —Cl | —CCl₃ | —O—S(O)₂CH₃ | |
| 7 | —Cl | —CHCl₂ | —S—C(O)N(CH₃)₂ | |
| 8 | —Cl | —CCl₃ | —OC(O)t-C₄H₉ | MP 67°–69° C. |
| 9 | —Cl | —CCl₃ | —OC(O)CH:CH₂ | RI = 1.5680 |
| 10 | —CF₃ | —CF₃ | —OC(S)N(C₂H₅)₂ | |
| 11 | —I | —CF₂Cl | —SC(S)N(n-C₄H₉)₂ | |
| 12 | —Cl | —CF₂Cl | —OC(O)—cyclo-C₄H₇ | |
| 13 | —Cl | —CCl₃ | 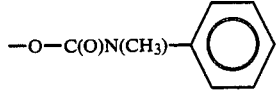 | RI = 1.5900 |
| 14 | —F | —CF₂Cl | 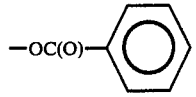 | |
| 15 | —Cl | —CCl₃ | 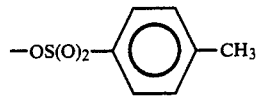 | RI = 1.5987 |
| 16 | —Cl | —CHCl₂ | —O—C(O)N(CH₃)C₃H₇ | |
| 17 | —Cl | —CCl₃ | 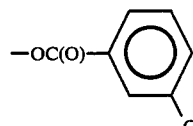 | RI = 1.5830 |
| 18 | —I | —CF₃ | —OC(O)H | |
| 19 | —CF₃ | —CHCl₂ | —OCOOCH₃ | |
| 20 | —CF₃ | —CF₃ | —OS(O)₂N(CH₃)₂ | |
| 21 | —F | —CFCl₂ |  | |
| 22 | —F | —CFCl₂ | —O—C(O)—CH₂Cl | |
| 23 | —Cl | —CCl₃ | —OC(O)NHnC₄H₉ | MP 79.5°–83.5° C. |
| 24 | —Cl | —CCl₃ | —O—C(O)NHC₂H₅ | MP 115°–123° C. |

*RI = refractive index n $\frac{25}{d}$ and MP = melting point.

The compounds of the present invention and formulations containing them have been found to be useful as plant fungicides especially valuable for the control of soil-borne, plant root disease organisms which attack the roots of plants. In accordance with the present invention, a method for protecting plants, which are in soil containing soil-borne, plant root disease organisms, from attack by said organisms is provided which comprises contacting plants or plant parts with a non-phytotoxic plant protecting amount of at least one of the compounds set forth hereinabove or with a composition (formulation) containing at least one of the compounds.

A practical advantage of the present method is that the active compounds or toxicants are used in amounts which are the equivalent of ounces of the active ingredient on a per acre basis as against the conventional soil fumigation practices which require pounds to hundreds of pounds of active material per acre.

In the present specification and claims, the term "systemic" defines the translocation of the active compounds employed in the present method within the plant. The active compounds can be applied either to the above-ground or preferably to below-ground portions of the plant.

In the present specification and claims, the term "plant part" is employed to designate all parts of a plant and includes seeds, bulbs, stolons, tubers, rhizomes, ratoons, corms, the root system hereinafter commonly referred to as root, the crown, stalk, stem, foliage or leaf system fruit or flower.

Compositions containing one or more of the active compounds of the present invention have been found to be very effective in the control of the plant diseases caused by Rhizoctonia and/or Pythium either before or after the plant has been attacked by said disease organisms.

Control of soil-borne plant disease by the present invention is achieved, for example, in cereal crops such as corn, wheat, barley, rye, oats, rice and sorghum; vegetable crops such as tomatoes, peppers, lettuce, onions, cabbage, broccoli, squash, cucumber, cauliflower, etc., legumes such as peanuts, soybeans, peas and alfalfa; root crops such as turnips, beets, carrots, white potatoes, sweet potatoes and yams; fiber crops such as cotton, flax and hemp; fruit crops such as apples, bananas, cantaloupes, cherries, dates, figs, grapes, pineapples, grapefruit, lemons, limes, oranges, peaches, pears, plums, strawberries and watermelon; oil crops such as castorbean, copra, olives, palms, rubber and sunflower; stimulants such as cocoa, coffee, tea and tobacco; sugar crops such as sugar cane and sugar beets; turf including bent grass and blue grass, rye and fescue; ornamentals such as chrysanthemums, zinnias, carnations, lilies, violets, petunias, marigolds, philodendrons, schefflera, dracaena, wax plants, jade plant, ivy, ferns, rubber plants, cactus and dieffenbachia; woody ornamentals such as pines, roses, rhododendron, azaleas, boxwood, spruce and the like. While the above lists a variety of crop plants which may be treated by the practice of the present invention, it is to be understood that the present method is not restricted to the above list of crop plants.

Generally in the actual practice of the method of the present invention, a non-phytotoxic plant protecting amount of the active toxicant compounds can be applied to the plant or plant part by a variety of convenient procedures. Such procedures include soil incorporation whereby compositions containing the active toxicant are mechanically mixed with the soil; applied to the surface of the soil and thereafter dragged, disced or rototilled into the soil; or transported into the soil with a liquid carrier such as by injection, spraying or irrigation. Additionally, a plant protecting amount of the active toxicant compounds can be employed in sprays, gels or coatings for above-ground applications or drenched onto the soil surface. In additional application methods, the active toxicant can be applied by vapor transfer; added in liquid or solid composition to hydroponic operations; seed treatment operations and by conventional plant part coating operations or other techniques known to those skilled in the art. The only limitation upon the mode of application employed is that it must be one which will allow the toxicant to come in contact with plants or plant parts.

The exact dosage of the active toxicant employed can be varied depending upon the specific plant, its stage of development, hardiness, the mode of application and its growth media. Generally, the active ingredient should be present in an amount equivalent to from about 50 micrograms to about 140 grams or more per plant on a per plant basis. Translating this into conventional application rates, this amount is equivalent to from about 0.0005 pound to about 10 pounds or more of the active ingredient on a per acre basis, as chemical available to the plant.

It will be appreciated that on a per plant basis, seed treatment of small seeded plant species such as grasses, carrots and the like will actually require much smaller amounts than 50 micrograms per plant. Generally, rates in the range of 1/32 to about 16 ounces per 100 pounds of seeds will be optimum for seed treatment among the diversity of plant species. For practices such as conventional tobacco transplant treatment or in-furrow soil treatment of plants such as soybeans at seeding and the like, an amount of active toxicant approximately equal to 0.05 to about 32 milligrams would be utilized on a per plant basis.

Larger amounts of the active ingredient may advantageously be applied when treatments are employed which distribute the material throughout the soil. For example, when the active ingredient is applied as an atplant row treatment or as an early or mid-season postplant side dress treatment, those amounts of chemical not proximal to plant roots are essentially unavailable to the plant and therefore not effective as set forth hereinabove. In such practices, the amount of the active ingredient employed needs to be increased to rates as high as about 20 pounds per acre or higher to assure that the requisite effective quantity of active ingredient is made available to the plants.

The present invention can be carried out by employing the pyridine compounds directly, either singly or in combination. However, the present invention also embraces the employment of liquids, dusts, waxes, gels, jellies, wettable powders, granules or encapsulated compositions containing at least one of said compounds as active ingredient. In such usage, the compound or compounds can be modified with one or more of a plurality of additaments or soil-modifying adjuvants including fertilizers, nematicides, herbicides, insecticides or other pesticidal adjuvants or inert solvents, inert liquid carriers and/or surface-active dispersing agents and coarsely or finely-divided inert solids. The augumented compositions are also adapted to be employed as concentrates and subsequently diluted with additional inert carrier to produce other compositions in the form of dusts, sprays, granules, washes or drenches. In compositions where the adjuvant is a coarsely or finely-divided solid, a surface-active agent or the combination of a surface-active agent and a liquid additament, the adjuvant cooperates with the active component so as to facilitate the invention. Whether the composition is employed in liquid, wettable powder, gel, wax, jelly, dust granule or encapsulated form, the active compound will normally be present in an amount of from about 2 to 98 percent by weight of the total composition.

In the preparation of dust, wettable powders or other solid compositions, the toxicant products can be compounded with any of the finely-divided solids, such as pyrophyllite, talc, chalk, gypsum, fullers's earth, bentonite, attapulgite, modified clays, starch, casein, gluten and the like. In such operations, the finely-divided carrier is ground or mixed with the toxicant or wet with a solution of the toxicant in a volatile organic solvent. Also, such compositions when employed as concentrates can be dispersed in water, with or without the aid of dispersing agents to form spray mixtures.

Granular formulations are usually prepared by impregnating a solution of the toxicant in a volatile organic solvent onto a bed of coarsely divided attapulgite, bentonite, diatomite or the like.

Additionally, gels containing the desired amount of one of the active compounds can be prepared by dispersing the active compound in an inert aqueous or organic based liquid and thereafter treating said mixture with a gelling medium such as crosslinked alkaline salts of polyacrylic acid, methyl cellulose, carboxymethyl cellulose, tertiarybutyl styrene, modified clays or other conventional gelling mediums.

Similarly, the toxicant products can be compounded with a suitable water-immiscible inert organic liquid and a surface-active dispersing agent to produce an emulsifiable concentrate which can be further diluted with water and oil to form spray mixtures in the form of oil-in-water emulsions. In such compositions, the carrier comprises an aqueous emulsion, i.e., a mixture of inert water-immiscible solvent, emulsifying agent and water. Preferred dispersing agents which can be employed in these compositions, are oil-soluble materials including non-ionic emulsifiers such as the condensation products of alkylene oxides with the inorganic acids, polyoxyethylene derivatives or sorbitan esters, complex ether alcohols and the like. Also, oil-soluble ionic emulsifying agents such as mahogany soaps can be used. Suitable inert organic liquids which can be employed in the compositions include vegetable oils or petroleum oils and distillates, toluene, liquid halohydrocarbons and synthetic organic oils. The surface-active dispersing agents are usually employed in liquid compositions and in the amount of from 0.1 to 20 percent by weight of the combined weight of the dispersing agent and active compound.

In addition, other compositions containing the desired amount of effective agent can be prepared by dispersing the toxicant in an inert organic liquid such as acetone, methylene chloride, chlorobenzene and petroleum distillates. The preferred inert organic solvent carriers are those which are adapted to accomplish the penetration and impregnation of the environment and particularly soil with the toxicant compounds and are of such volatility as to leave little permanent residue thereon. Particularly desirable carriers are the petroleum distillates boiling almost entirely under 400° F. at atmospheric pressure and having a flash point above 80° C. The proportion of the compounds of this invention employed in a suitable solvent may vary from about 2 to about 50 percent or higher. Additionally, the active components can be compounded with waxes or petroleum jellies to prepare viscous or semi-solid treating compositions.

A preferred liquid composition includes the use of the active compound or compounds in combination with surface-active dispersant agents only. In such compositions, it is preferred to use ionic and non-ionic blends of such dispersant agents in combination with one or more of the active materials. A particular advantage of such a formulation is that phytotoxicity associated with certain inert solvents, such as, xylene, methylene chloride and like materials can be avoided. Generally, the use of such formulations will result in compositions containing 75 percent or more of the active component.

Owing to the excellent suspensibility of the above formulation in water, it is convenient and often preferred to prepare and use aqueous concentrates as stock solutions themselves. In such practices, minor agitation results in a practical, stable formulation very adaptable for use in its concentrate form to treat soil in sprays or drenches. Additionally, if desired, the concentrates can be easily diluted with additional water for use as foliar spray treatments, soil drench treatments and the like.

Water miscible organic solvents such as lower alcohols or propylene glycol can be added to depress the freezing point and further cooperate with the above system in that they are essentially non-phytotoxic.

The expression "soil" is employed herein in its broadest sense to be inclusive of all conventional soils, as defined in Webster's New International Dictionary, Second Edition, Unabridged published in 1937, G. C. Merriam Co, Springfield, Mass. Thus, the term refers to any substance or medium in which plants may take root and grow and is intended to include not only earth, but also compost, manure, muck, sand, synthetic growth mediums such as vermiculite and pearlite and the like, adapted to support plant growth.

DESCRIPTION OF THE PREFERRED UTILITY EMBODIMENTS

In order that the present invention may be more fully understood, the following examples are given to illustrate the manner by which the active compound can be employed.

EXAMPLE III

Acetone dispersions were prepared by admixing predetermined amounts of one of the active compounds with predetermined amounts of acetone.

Soil infected with the causative disease organism of root rot and seedling damping off, i.e., *Rhizoctonia solani* was uniformly mixed and placed in 3-inch pots. Cotton seeds of the variety "Acala SJ-2" were uniformly treated with an amount of the above acetone dispersions equivalent to treating 100 pounds of seeds with eight ounces of the active compound. Ten seeds were planted in each pot. Additional seeds which had been treated with acetone alone were also planted to serve as controls. After planting, the pots containing the seeds were maintained under greenhouse conditions conducive to both plant growth and disease development. About twenty-four days after treatment, the pots were examined to determine the percent of the cotton plants surviving. The results of this examination are set forth below in Table II.

TABLE II

| Compound Number | Percent of cotton plants surviving after growing 18 days in soil infected with *Rhizoctonia solani* |
|---|---|
| 1 | 92 |
| 3 | 58 |
| 8 | 96 |
| 9 | 63 |
| 13 | 33 |
| 15 | 46 |
| 17 | 4 |
| Control | 0 |

EXAMPLE IV

Acetone dispersions were prepared by admixing predetermined amounts of one of the active compounds with predetermined amounts of acetone.

Soil infected with the causative disease organism of root rot and seedling damping off, i.e., *Rhizoctonia solani* was uniformly mixed and placed in 3-inch pots. Cotton seeds of the variety "Acala SJ-2" were uniformly treated with predetermined amounts of the above acetone dispersions. Ten seeds were planted in each pot. Additional seeds which had been treated with acetone alone were also planted to serve as controls. After planting, the pots containing the seeds were maintained under greenhouse conditions conducive to both plant growth and disease development. At seven and thirty-three days after planting, the pots were examined to determine the kill and control of the above-indicated disease organism. The results of this examination are set forth below in Table III.

TABLE III

| Compound Number | Dosage of treatment in ounces per hundred Pounds of Seeds | Percent kill and control of Rhizoctonia solani at indicated days after planting | |
|---|---|---|---|
| | | 7 | 33 |
| 2 | 8 | 100 | 74 |
| | 2 | 53 | 37 |
| 3 | 8 | 100 | 74 |
| | 2 | 89 | 68 |
| 13 | 8 | 95 | 63 |
| | 2 | 32 | 16 |
| 15 | 8 | 89 | 84 |
| | 2 | 17 | 16 |
| 17 | 8 | 26 | 0 |
| | 2 | 37 | 16 |
| 23 | 8 | 79 | 74 |
| | 2 | 79 | 58 |
| 24 | 8 | 79 | 42 |
| | 2 | 53 | 32 |
| Control | — | 0 | 0 |

EXAMPLE V

Acetone dispersions were prepared by admixing predetermined amounts of one of the active compounds with predetermined amounts of acetone.

Soil infected with the causative disease organism of seedling damping off, i.e., *Pythium ultimum* was uniformly mixed and placed in; 3-inch pots. Pea seeds of the variety "Little Marvel" were uniformly treated with predetermined amounts of the above acetone dispersions. Ten seeds were planted in each pot with 5 replicates. Additional seeds which had been treated with acetone alone were also planted to serve as controls. After planting, the pots containing the seeds were maintained under greenhouse conditions conducive to both plant growth and disease development. After 16 days, the pots were examined to determine the percentage of the seeds to emerge. The compounds, the dosage and the percent emergence are set forth below in Table IV.

TABLE IV

| Compound Number | Percent emergence of Pea seeds treated at the indicated dosage rate in ounces of compounds per 100 pounds of seeds | |
|---|---|---|
| | 2 ounces | 4 ounces |
| 1 | 8 | 2 |
| 3 | 4 | 22 |
| 8 | 2 | 4 |
| 23 | 0 | 12 |
| Control | 0 | 0 |

EXAMPLE VI

Acetone dispersions were prepared by admixing predeterm amounts of one of the active compounds with predetermined amounts of acetone.

Soil infected with the causative disease organism of root rot and seedling damping off, i.e., *Pythium ultimum* was uniformly mixed and placed in 3-inch pots. Cotton seeds of the variety "Acala SJ-2" were uniformly treated with predetermined amounts of the above acetone dispersions. Ten seeds were planted in each pot. Additional seeds which had been treated with acetone alone were also planted to serve as controls. After planting, the pots containing the seeds were maintained under greenhouse conditions conducive to both plant growth and disease development. After 16 days, the pots were examined to determine the percentage of the seeds to emerge. The compounds, the dosage and the percent emergence are set forth below in Table V.

TABLE V

| Compound Number | Percent emergence of cotton seeds treated at the indicated dosage rate in ounces of compound per 100 pounds of seeds | |
|---|---|---|
| | 2 ounces | 4 ounces |
| 1 | 86 | 79 |
| 3 | 52 | 79 |
| 8 | 72 | 76 |
| 23 | 41 | 76 |
| Control | 0 | 0 |

EXAMPLE VII

Acetone dispersions were prepared by admixing predeterm amounts of one of the active compounds with predetermined amounts of acetone.

Soil infected with the causative disease organism of root rot and seedling damping off, i.e., *Rhizoctonia solani* was uniformly mixed and placed in 3-inch pots. Cotton seeds of the variety "Acala SJ-2" were uniformly treated with predetermined amounts of the above acetone dispersions. Ten seeds were planted in each pot. Additional seeds which had been treated with acetone alone were also planted to serve as controls. After planting, the pots containing the seeds were maintained under greenhouse conditions conducive to both plant growth and disease development. At seven and eleven days after planting, the pots were examined to determine the kill and control of the above-indicated disease organism. The results of this examination are set forth below in Table VI.

TABLE VI

| Compound Number | Dosage of treatment in ounces per hundred Pounds of Seeds | Percent kill and control of Rhizoctonia solani at indicated days after planting | |
|---|---|---|---|
| | | 7 | 11 |
| 2 | 8 | 100 | 83 |
| | 2 | 50 | 33 |
| 3 | 8 | 100 | 100 |
| | 2 | 89 | 83 |
| 13 | 8 | 94 | 83 |
| | 2 | 28 | 22 |
| 15 | 8 | 89 | 83 |
| | 2 | 17 | 11 |
| 17 | 8 | 22 | 0 |
| | 2 | 33 | 11 |
| 23 | 8 | 78 | 83 |
| | 2 | 78 | 72 |
| 24 | 8 | 78 | 50 |
| | 2 | 50 | 39 |
| Control | — | 0 | 0 |

What is claimed is:
1. A compound corresponding to the formula

4,670,045

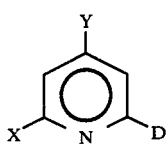

wherein
X represents bromo, chloro, fluoro, iodo or trifluoromethyl; Y represents —CCl₃, —CF₃, —CHCl₂, —CFCl₂ or —CF₂Cl; D represents

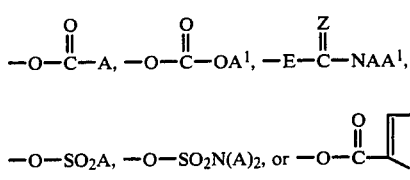

wherein Z represents oxygen or sulfur; E represents oxygen or sulfur with the proviso that E can be sulfur only if Y is CF₃; each A independently represents hydrogen, alkyl of 1 to 4 carbon atoms, alkenyl of 2 to 4 carbon atoms, phenyl or benzyl and A¹ represents alkyl of 1 to 4 carbon atoms, alkenyl of 2 to 4 carbon atoms, phenyl or benzyl.

2. A compound as defined in claim 1 wherein X is chloro.

3. A compound as defined in claim 2 wherein Y is —CCl₃.

4. The compound as defined in claim 3 which is 6-chloro-4-(trichloromethyl)-2-pyridinyl ethyl carbonate.

5. The compound as defined in claim 3 which is 6-chloro-4-(trichloromethyl)-2-pyridinyl pentanoate.

6. The compound as defined in claim 3 which is 6-chloro-4-(trichloromethyl)-2-pyridinyl 2,2-dimethylpropanoate.

7. The compound as defined in claim 3 which is 6-chloro-4-(trichloromethyl)-2-pyridinyl propenoate.

8. The compound as defined in claim 3 which is 6-chloro-4-(trichloromethyl)-2-pyridinyl 2-furancarboxylate.

9. The compound as defined in claim 3 which is 6-chloro-4-(trichloromethyl)-2-pyridinyl benzoate.

10. The compound as defined in claim 3 which is 6-chloro-4-(trichloromethyl)-2-pyridinyl 4-methylbenzenesulfonate.

11. The compound as defined in claim 3 which is 6-chloro-4-(trichloromethyl)-2-pyridinyl methylcarbamate.

12. The compound as defined in claim 3 which is 6-chloro-4-(trichloromethyl)-2-pyridinyl ethylcarbamate.

13. The compound as defined in claim 3 which is 6-chloro-4-(trichloromethyl)-2-pyridinyl butylcarbamate.

14. A composition comprising an inert adjuvant in intimate admixture with from about 2 to about 98 percent by weight of a compound corresponding to the formula

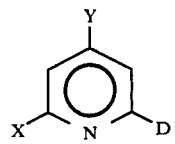

wherein
X represents bromo, chloro, fluoro, iodo or trifluoromethyl; Y represents —CCl₃, —CF₃, —CHCl₂, —CFCl₂ or —CF₂Cl; D represents

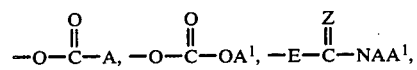

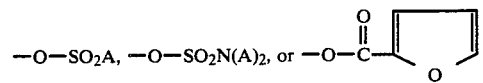

wherein Z represents oxygen or sulfur; E represents oxygen or sulfur with the proviso that E can be sulfur only if Y is CF₃; each A independently represents hydrogen, alkyl of 1 to 4 carbon atoms, alkenyl of 2 to 4 carbon atoms, phenyl or benzyl and A1 represents alkyl of 1 to 4 carbon atoms, alkenyl of 2 to 4 carbon atoms, phenyl or benzyl.

15. A composition as defined in claim 14 wherein in the active compound X is chloro.

16. A composition as defined in claim 15 wherein the active compound Y is —CCl₃.

17. A composition as defined in claim 16 wherein the active compound is 6-chloro-4-(trichloromethyl)-2-pyridinyl ethyl carbonate.

18. A composition as defined in claim 16 wherein the active compound is 6-chloro-4-(trichloromethyl)-2-pyridinyl pentanoate.

19. A composition as defined in claim 16 wherein the active compound is 6-chloro-4-(trichloromethyl)-2-pyridinyl 2,2-dimethylpropanoate.

20. A composition as defined in claim 16 wherein the active compound is 6-chloro-4-(trichloromethyl)-2-pyridinyl propenoate.

21. A composition as defined in claim 16 wherein the active compound is 6-chloro-4-(trichloromethyl)-2-pyridinyl 2-furancarboxylate.

22. A composition as defined in claim 16 wherein the active compound is 6-chloro-4-(trichloromethyl)-2-pyridinyl benzoate.

23. A composition as defined in claim 16 wherein the active compound is 6-chloro-4-(trichloromethyl)-2-pyridinyl 4-methylbenzenesulfonate.

24. A composition as defined in claim 16 wherein the active compound is 6-chloro-4-(trichloromethyl)-2-pyridinyl methylcarbamate.

25. A composition as defined in claim 16 wherein the active compound is 6-chloro-4-(trichloromethyl)-2-pyridinyl ethylcarbamate.

26. A composition as defined in claim 16 wherein the active compound is 6-chloro-4-(trichloromethyl)-2-pyridinyl butylcarbamate.

27. A method for protecting plants from plant fungal disease organisms which attack the plant root system which comprises contacting plants, plant parts or their habitat with a non-phytotoxic, fungicidally effective amount of a composition which comprises an inert adjuvant in intimate admixture with an active compound corresponding to the formula

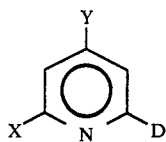

wherein
X represents bromo, chloro, fluoro, iodo or trifluoromethyl;
Y represents —CCl$_3$, —CF$_3$, —CHCl$_2$ or —CF$_2$Cl;
D represents

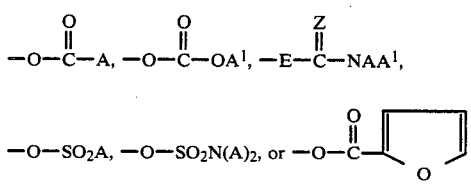

wherein Z represents oxygen or sulfur; E represents oxygen or sulfur with the proviso that E can be sulfur only if Y is CF$_3$; each A independently represents hydrogen, alkyl of 1 to 4 carbon atoms, alkenyl of 2 to 4 carbon atoms, phenyl or benzyl and A$^1$ represents alkyl of 1 to 4 carbon atoms, alkeryll of 2 to 4 carbon atoms, phenyl or benzyl.

28. A method as defined in claim 27 wherein in the active compound X is chloro.

29. A method as defined in claim 28 wherein in the active compound Y is —CCl$_3$.

30. A method as defined in claim 29 wherein the active compound is 6-chloro-4-(trichloromethyl)-2-pyridinyl ethyl carbonate.

31. A method as defined in claim 29 wherein the active compound is 6-chloro-4-(trichloromethyl)-2-pyridinyl pentanoate.

32. A method as defined in claim 29 wherein the active compound is 6-chloro-4-(trichloromethyl)-2-pyridinyl 2,2-dimethylpropanoate.

33. A method as defined in claim 29 wherein the active compound is 6-chloro-4-(trichloromethyl)-2-pyridinyl propenoate.

34. A method as defined in claim 29 wherein the active compound is 6-chloro-4-(trichloromethyl)-2-pyridinyl 2-furancarboxylate.

35. A method as defined in claim 29 wherein the active compound is 6-chloro-4-(trichloromethyl)-2-pyridinyl benzoate.

36. A method as defined in claim 29 wherein the active compound is 6-chloro-4-(trichloromethyl)-2-pyridinyl 4-methylbenzenesulfonate.

37. A method as defined in claim 29 wherein the active compound is 6-chloro-4-(trichloromethyl)-2-pyridinyl methylcarbamate.

38. A method as defined in claim 29 wherein the active compound is 6-chloro-4-(trichloromethyl)-2-pyridinyl ethylcarbamate.

39. A method as defined in claim 29 wherein the active compound is 6-chloro-4-(trichloromethyl)-2-pyridinyl butylcarbamate.

* * * * *